(12) United States Patent  
Jimenez (10) Patent No.: US 8,032,967 B2
(45) Date of Patent: Oct. 11, 2011

(54) POWERED TOOTHBRUSH WITH TWO-SIDED MOVING HEAD

(75) Inventor: Eduardo J. Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 1267 days.

(21) Appl. No.: 11/672,979

(22) Filed: Feb. 9, 2007

(65) Prior Publication Data

US 2008/0189886 A1 Aug. 14, 2008

(51) Int. Cl.
*A61C 17/34* (2006.01)
(52) U.S. Cl. ............... 15/110; 15/111; 15/22.1; 15/22.4
(58) Field of Classification Search ............... 15/221, 15/22.1, 22.2, 22.4, 110, 111
See application file for complete search history.

(56) References Cited

U.S. PATENT DOCUMENTS

| 1,566,547 | A | * | 12/1925 | Luzzi | 601/108 |
|---|---|---|---|---|---|
| D287,072 | S | * | 12/1986 | Pfleger | D4/104 |
| 5,974,613 | A | | 11/1999 | Herzog | |
| 6,347,425 | B1 | | 2/2002 | Fattori et al. | |
| 6,725,490 | B2 | * | 4/2004 | Blaustein et al. | 15/22.2 |
| 6,760,946 | B2 | | 7/2004 | DePuydt | |
| 6,779,851 | B2 | * | 8/2004 | Bouchiere | 300/21 |
| 6,829,801 | B2 | | 12/2004 | Schutz | |
| 6,892,413 | B2 | * | 5/2005 | Blaustein et al. | 15/22.2 |
| 6,895,629 | B1 | * | 5/2005 | Wenzler | 15/106 |
| 6,907,636 | B2 | | 6/2005 | Hafemann | |
| D514,320 | S | | 2/2006 | Hohlbein | |
| RE39,185 | E | * | 7/2006 | Noe et al. | 15/104.94 |
| 7,073,225 | B1 | * | 7/2006 | Ford | 15/167.2 |
| 7,124,461 | B2 | * | 10/2006 | Blaustein et al. | 15/22.2 |
| 7,143,462 | B2 | * | 12/2006 | Hohlbein | 15/111 |
| 7,386,905 | B2 | * | 6/2008 | Eliav et al. | 15/22.1 |
| D602,695 | S | * | 10/2009 | Koye | D4/107 |
| 7,614,111 | B2 | * | 11/2009 | Moskovich et al. | 15/167.1 |
| 7,721,376 | B2 | * | 5/2010 | Hohlbein et al. | 15/111 |
| 2003/0079305 | A1 | | 5/2003 | Takahata et al. | |
| 2003/0126700 | A1 | * | 7/2003 | Jeng et al. | 15/28 |
| 2003/0140437 | A1 | * | 7/2003 | Eliav et al. | 15/22.2 |
| 2003/0154568 | A1 | | 8/2003 | Boland et al. | |
| 2003/0226223 | A1 | * | 12/2003 | Chan | 15/22.2 |
| 2004/0016067 | A1 | | 1/2004 | Kraemer | |
| 2004/0134007 | A1 | | 7/2004 | Davies | |

(Continued)

FOREIGN PATENT DOCUMENTS

EP 1733699 A 12/2006

(Continued)

OTHER PUBLICATIONS

Interntional Search Report Dated Jul. 22, 2008.

*Primary Examiner* — Shay Karls
(74) *Attorney, Agent, or Firm* — Judy W. Chung (57) ABSTRACT

A powered toothbrush includes a handle having a neck. A head is mounted to the neck and has a first surface and an opposed second surface. A first tuft block is mounted to the head, with the tuft block having tooth cleaning elements extending outwardly from the first surface. A tissue cleanser is mounted to the head and has a plurality of tissue engaging elements extending outwardly from the second surface. A drive assembly configured to cause the first tuft block and the tissue cleanser to move with respect to the head.

23 Claims, 5 Drawing Sheets

U.S. PATENT DOCUMENTS

| | | |
|---|---|---|
| 2004/0168269 A1 | 9/2004 | Kunita et al. |
| 2004/0168272 A1* | 9/2004 | Prineppi ........................... 15/28 |
| 2004/0255416 A1* | 12/2004 | Hohlbein ....................... 15/106 |
| 2005/0000049 A1 | 1/2005 | Hohlbein |
| 2005/0011023 A1 | 1/2005 | Chan |
| 2005/0091769 A1 | 5/2005 | Jimenez et al. |
| 2005/0210612 A1 | 9/2005 | Hohlbein et al. |
| 2006/0010623 A1 | 1/2006 | Crossman et al. |
| 2006/0010628 A1 | 1/2006 | Moskovich |
| 2006/0026784 A1* | 2/2006 | Moskovich et al. ............ 15/110 |
| 2006/0057087 A1* | 3/2006 | Moskovich et al. ............ 424/65 |
| 2006/0064833 A1* | 3/2006 | Jacobs ........................... 15/110 |
| 2006/0085932 A1 | 4/2006 | Santos |
| 2006/0117506 A1 | 6/2006 | Gavney, Jr. |
| 2008/0176183 A1* | 7/2008 | Gatzemeyer et al. ........... 433/82 |

FOREIGN PATENT DOCUMENTS

| | | |
|---|---|---|
| WO | 2004028294 A | 4/2004 |
| WO | 2006055571 A | 5/2006 |

* cited by examiner

POWERED TOOTHBRUSH WITH TWO-SIDED MOVING HEAD

FIELD OF THE INVENTION

This invention relates generally to a powered toothbrush and, in particular, to a powered toothbrush having a head with moving tooth cleaning elements and a moving tooth cleanser.

BACKGROUND OF THE INVENTION

As toothbrush design has evolved in an effort to improve cleaning of teeth and gums, the complexity of toothbrushes and their functions have increased. Powered toothbrushes are one example of efforts to improve tooth cleaning by including one or more movable sets of cleaning elements.

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can be lead bad breath or oral malodor.

Consequently, tissue cleansers have been added to a face of the head of a conventional toothbrush opposite the face on which the tooth cleaning elements are positioned.

It would be desirable to provide a powered toothbrush with a tooth cleanser that reduces or overcomes some or all of the difficulties inherent in prior known devices. Particular objects and advantages will be apparent to those skilled in the art, that is, those who are knowledgeable or experienced in this field of technology, in view of the following disclosure of the invention and detailed description of certain embodiments.

SUMMARY

The principles of the invention may be used to advantage to provide a powered toothbrush having a head with moving tooth cleaning elements and a moving tooth cleanser. In accordance with a first aspect, a powered toothbrush includes a handle having a neck. A head is mounted to the neck and has a first surface and an opposed second surface. A first tuft block is mounted to the head, with the tuft block having tooth cleaning elements extending outwardly from the first surface. A tissue cleanser is mounted to the head and has a plurality of tissue engaging elements extending outwardly from the second surface. A drive assembly configured to cause the first tuft block and the tissue cleanser to move with respect to the head.

In accordance with another aspect, a powered toothbrush includes a handle having a neck. A head is mounted to the neck and has a first surface and an opposed second surface. A first tuft block is mounted to the head, with the first tuft block having tooth cleaning elements extending outwardly from the first surface and a tuft block base portion having a first slot formed therein. A tissue cleanser is mounted to the head and has a plurality of projections extending outwardly from the second surface and a tissue cleanser base portion having a second slot formed therein. A power source is mounted inside the handle. A motor is operably connected to the power source. A drive shaft is rotatably driven by the motor and has an offset portion that engages each of the first slots of the tuft block base portion and tissue cleanser base portion to drive the first tuft block and tissue cleanser in an oscillating mann In accordance with a further aspect, a powered toothbrush includes a handle having a neck. A head is mounted to the neck and has a first surface and an opposed second surface. A first tuft block is mounted to the head, with the first tuft block having bristles extending outwardly from the first surface and a tuft block base portion having a first slot formed therein. A tissue cleanser is mounted to the head and has a plurality of nubs extending outwardly from the second surface and a tissue cleanser base portion having a second slot formed therein. A battery is mounted inside the handle. A motor is operably connected to the battery. A drive shaft is rotatably driven by the motor and has an offset portion that engages each of the first slots of the tuft block base portion and tissue cleanser base portion to drive the first tuft block and tissue cleanser in an oscillating manner.

Substantial advantage is achieved by providing a powered toothbrush having a head with moving tooth cleaning elements and a moving tooth cleanser. In particular, certain embodiments of the toothbrush provide enhanced cleaning as well as reducing bad breath and oral malodor.

These and additional features and advantages disclosed here will be further understood from the following detailed disclosure of certain embodiments.

BRIEF DESCRIPTION OF THE DRAWINGS

FIG. 1 is a sectional bottom view of a toothbrush.

The figures referred to above are not drawn necessarily to scale and should be understood to provide a representation of the invention, illustrative of the principles involved. Some features of the powered toothbrush depicted in the drawings have been enlarged or distorted relative to others to facilitate explanation and understanding. The same reference numbers are used in the drawings for similar or identical components and features shown in various alternative embodiments. Powered toothbrushes as disclosed herein would have configurations and components determined, in part, by the intended application and environment in which they are used.

DETAILED DESCRIPTION OF CERTAIN PREFERRED EMBODIMENTS

Referring to the drawings, in FIG. 1 a toothbrush includes a handle 12 at a first end of the toothbrush, a head 14 at a second end of the toothbrush, and a neck 15 positioned between the handle 12 and the head 14, a rotatable shaft 16 extending from handle 12 to head 14. Handle 12 provides compartments for holding a drive assembly 19 including an electric motor 20 and a power source 21. In certain embodiments, power source 21 is formed of two batteries 22, 24. A shaft coupling 26 is arranged to grip one end of shaft 16 and allow the shaft to be pulled out for cleaning or replacement.

Head 14 may be replaceable, or it may be permanently attached to handle 12. Head 14 includes a plurality of tooth cleaning elements on a first surface 18 thereof. As use herein, the term "tooth cleaning elements" includes any type of structure that is commonly used or is suitable for use in providing oral health benefits (e.g., tooth cleaning, tooth polishing, tooth whitening, massaging, stimulating, etc.) by making intimate contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members. The tooth cleaning elements may be arranged on head 14 in any configuration.

In the embodiment illustrated herein, head 14 includes bristle tufts, which may be formed with bristles of the same or different bristle materials (such as nylon bristles, spiral bristles, rubber bristles, etc.). Moreover, while the tooth cleaning elements of head 14 may be arranged so that they are generally perpendicular to first surface 18 of head 14, some or all of the tooth cleaning elements may be angled at various angles with respect to the first surface 18. When first surface 18 includes bristle tufts, it is thereby possible to select the combination of bristles configurations, bristle materials and bristle orientations to achieve specific intended results and operational characteristics, thus maximizing and enhancing cleaning, tooth polishing, tooth whitening, massaging, and stimulation.

The tooth cleaning elements may be arranged by any conventional method. For example, the tooth cleaning elements may be stapled to head 14. In certain embodiments, the tooth cleaning elements in the form of strands or bristles can be attached via in-molded technology (IMT) methods that generally require small cross-sections of material into which the strands are permanently attached. The strands utilizing IMT methods may be attached during formation of the handle 12 or during formation of head 14, which is the portion of toothbrush 10 to which the strands and other materials are attached.

In other embodiments, tooth cleaning elements in the form of strands or bristles may be attached via anchor free tufting (AFT). In the AFT brush making process, described in detail in U.S. Pat. No. 6,779,851, nylon is fed into a pre-molded plate that can be made from any thermoplastic or elastomer material or combination thereof. This nylon may be processed into bristle tufts of various sizes and shapes. The non-use or proximal end of the nylon is heated and melted to retain the nylon in the brush head when a reasonable pulling force is applied. This head plate may then be ultrasonically welded to a pre-molded handle that has a peripheral wall or frame on which the head plate will rest and become fused to the handle.

Figure 2:
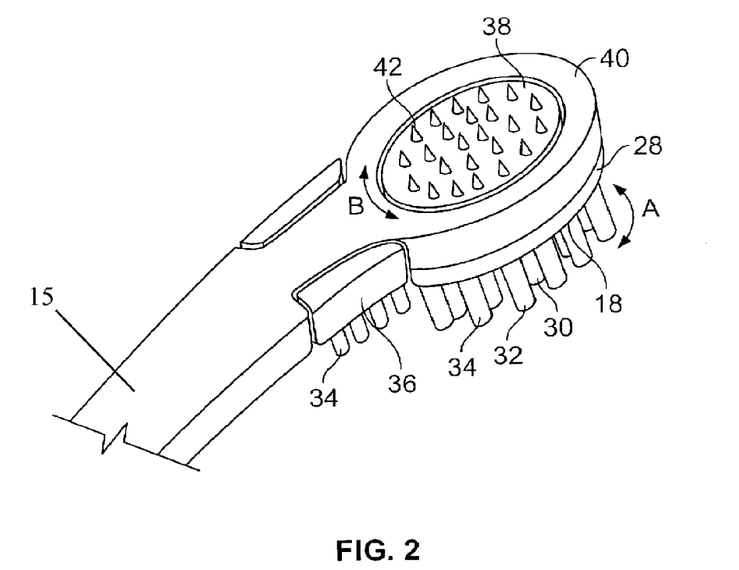
FIG. 2 is a perspective top view of the head of the toothbrush of FIG. 1.

In certain embodiments, head 14 includes a first tuft block 28 at a distal end thereof. In the illustrated embodiment, first tuft block 28 includes an inner ring 30 and an outer ring 32, each of which includes a plurality of tufts of bristles 34. It is to be appreciated that other shapes for first tuft block 28 are considered to be within the scope of the invention, such as egg or oval shapes, or any other suitable shape. First tuft block 28 is operably connected to shaft 16 such that first tuft block 28 is rotated in oscillating fashion back and forth in the direction of arrow A, as described in greater detail below.

A second tuft block 36 may be positioned between first tuft block 28 and neck 15 of toothbrush 10. Second tuft block 36 has a plurality of tooth cleaning elements such as tufts of bristles 34.

A tissue cleanser 38 is provided on a second surface 40 of head 14 opposite that of first surface. Tissue cleanser 38 is operably connected to shaft 16 such that tissue cleanser 38 is rotated in oscillating fashion back and forth in the direction of arrow B, as described in greater detail below.

Tissue cleanser 38 may be formed of an elastomeric material, such as a biocompatible resilient material suitable for uses in an oral hygiene apparatus. To provide improved comfort as well as cleaning benefits, the elastomeric material preferably has a hardness property in the range of A8 to A25 Shore hardness. As an example, one embodiment of an elastomeric material is styrene-ethylene/butylene-styrene block copolymer (SEBS) manufactured by GLS Corporation. It is to be appreciated that SEBS material from other manufacturers, or other materials within and outside the noted hardness range could be used. Suitable materials for tissue cleanser 38 will become readily apparent to those skilled in the art, given the benefit of this disclosure.

Tissue cleanser 38 may be configured with a plurality of tissue engaging elements 42, which may be formed as nubs. As used herein a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection), the base width can be substantially larger than the height. Various embodiments of suitable tissue engaging elements are described in commonly owned U.S. Pat. No. 7,143,462, entitled "Oral Care Implement," the entire disclosure of which is hereby incorporated by reference in its entirety.

Nubs 42 are designed to significantly reduce a major source of bad breath in people and improve hygiene. Nubs 42 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, nubs 42 provide for gentle engagement with the soft tissue while reaching downward into the recesses of adjacent papillae of the tongue. The elastomeric construction of nubs 42 also enables them to follow the natural contours of the oral tissue surfaces, such as the tongue, cheeks, lips, and gums of a user. Moreover, the soft nubs 42 are able to flex as needed to traverse and clean the soft tissue surfaces in the mouth along which they are moved.

Figure 3:
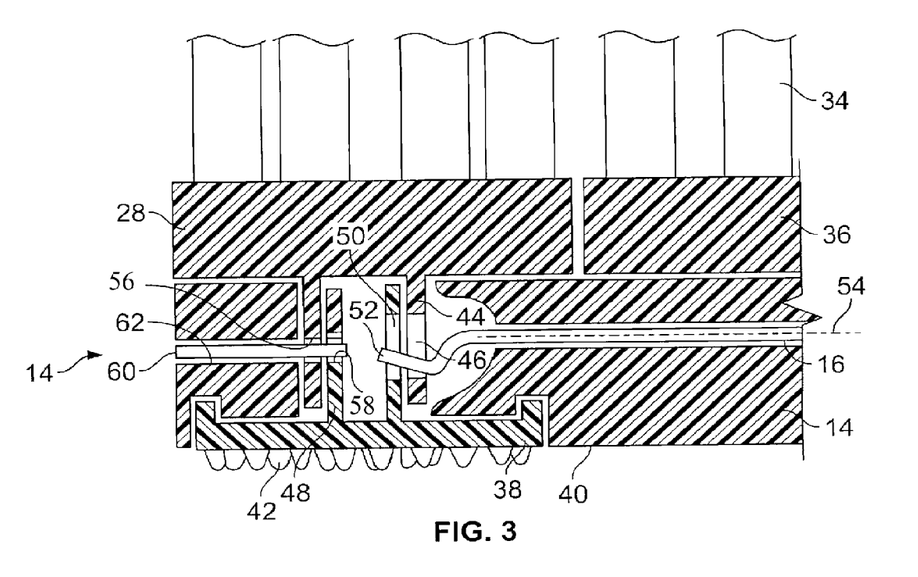
FIG. 3 is a section view of a portion of the head of the toothbrush of FIG. 1.

First tuft block 28 has a base portion 44 having a first slot 46 formed therein. Tissue cleanser 38 also includes a base portion 48 having a first slot 50 formed therein. In the illustrated embodiment, base portion 44 of first tuft block 28 and base portion 48 of tissue cleanser 38 are substantially cylindrical, are nested with one another concentrically such that first slot 46 of first tuft block 28 and first slot 50 tissue cleanser 38 are aligned with one another. In the illustrated embodiment, base portion 48 of tissue cleanser 38 has a smaller external diameter than the internal diameter of base portion 44 of first tuft block 28 such that base portion 48 of tissue cleanser 38 is nested within base portion 44 of first tuft block 28. It is to be appreciated, however, that head 14 could be configured such that base portion 44 of first tuft block 28 is nested within base portion 48 of tissue cleanser 38.

Shaft 16 has a remote-most end 52 that is off-set from a central longitudinal axis 54 of shaft 16. Remote-most end 52 extends into first slot 46 of first tuft block 28 and first slot 50 of tissue cleanser 38. When shaft 16 is rotated by motor 20, remote end 36 describes a circle about shaft 16 and drivingly engages first slot 46 of first tuft block 28 and first slot 50 of tissue cleanser 38 to cause both first tuft block 28 and tissue cleanser 38 to move in an oscillating fashion. The width of first slot 46 of first tuft block 28 and first slot 50 of tissue cleanser 38 may be generally the same as the diameter of remote-most end 52 to leave minimum play; thus keeping noise to a minimum during use. Shaft 16 is preferably of unitary, that is, one-piece construction, and is formed of a single length of a thin rod and shaped as shown. However, it is possible to arrange for remote-most end 52 to be separately formed or provided and fixed to a straight end part of shaft 16.

In certain embodiments, base portion 44 of first tuft block 28 includes a second slot 56, and base portion 48 of tissue cleanser includes a second slot 58, which are aligned with one another. A pin 60 is inserted through an aperture 62 in head 14, and extends into second slots 56, 58. Pin 60 secures first tuft block 28 and tissue cleanser 38, preventing them from being axially displaced from head 14. Other suitable devices and/or methods of securing first tuft block 28 and tissue cleanser 38 to head 14 are considered to be within the scope of the present invention, and other such suitable devices and/or methods will become readily apparent to those skilled in the art, given the benefit of this disclosure.

Figure 4:
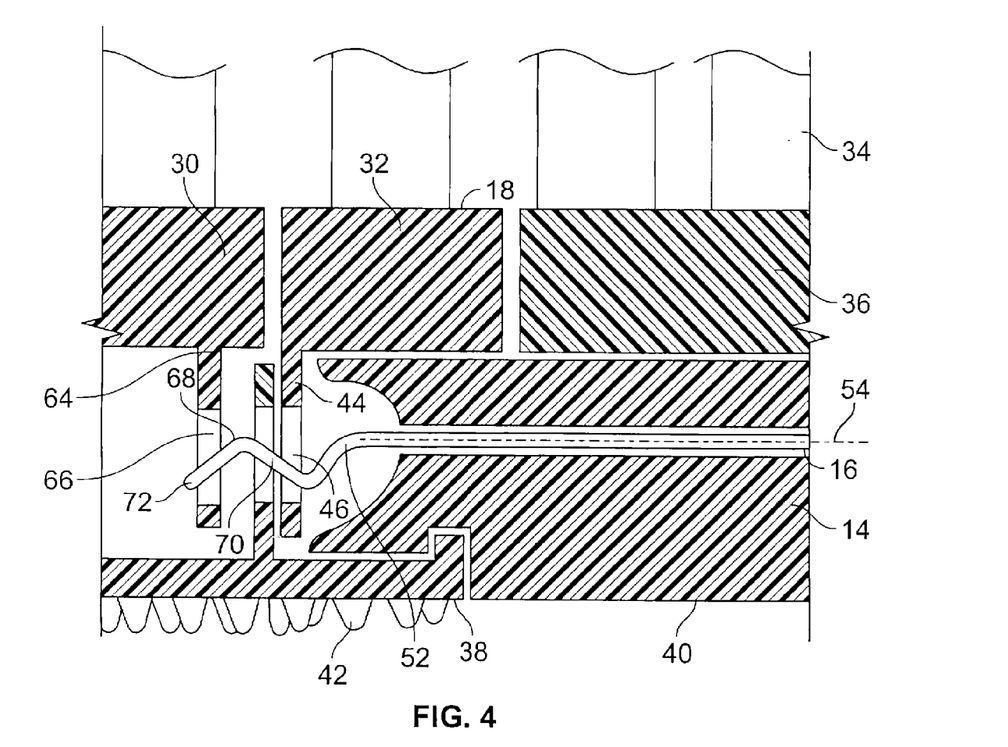
FIG. 4 is a section view of a portion of an alternative embodiment of a head of the toothbrush of FIG. 1.

In certain embodiments, as seen in FIG. 4, first tuft block 28 has a second base portion 64 to which inner ring 30 is secured, with a slot 66 formed therein. Outer ring 32 is secured to base portion 44. Remote-most end 52 of shaft 16 includes a V-shaped segment 68, which is oriented eccentrically with respect to the axis of rotation. A first inclined arm 70 of segment 68 engages first slots 46, 50 of base portions 44, 48, and a second inclined arm 72 engages slot 66 of second base portion 64. As shaft rotates, the eccentric rotational movement of segment 68 causes outer ring 32, along with tissue cleanser 38 to rotate in oscillating fashion in a first direction while inner ring 30 rotates in oscillating fashion in a second opposite direction.

Figure 5:
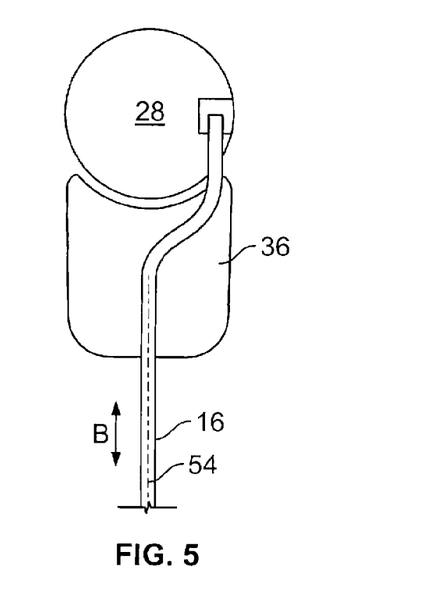
FIG. 5 is a bottom plan view of an alternative embodiment of a portion of the head of the toothbrush of FIG. 1.

In certain embodiments, second tuft block 36 is configured to be movable with respect to head 14. In the embodiment illustrated in FIG. 5, shaft 16 is fixed to second tuft block 36 and moves in reciprocating manner in a linear fashion in the direction of arrow B, parallel to longitudinal axis 54 of shaft 16. Thus, as shaft 16 reciprocates or oscillates, second tuft block 36 is driven in oscillating fashion in the direction of arrow B, parallel to longitudinal axis 54. A projection 74 on the end of remote-most end 52 engages a slot 76 formed in first tuft block 28 to drive first tuft block 28 in oscillating fashion.

Figure 6:
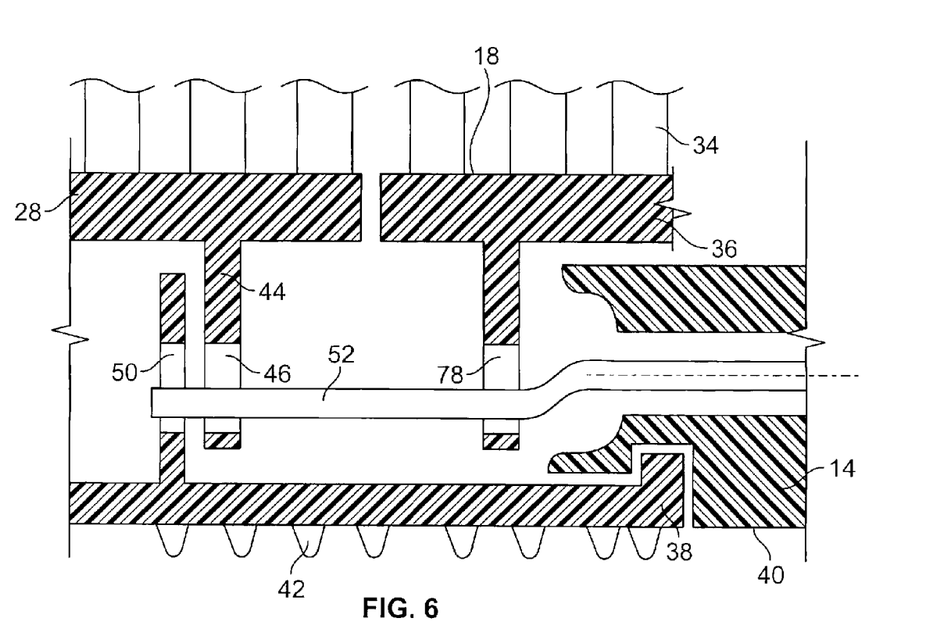
FIG. 6 is a section view of a portion of an alternative embodiment of a head of the toothbrush of FIG. 1.

In another embodiment, illustrated in FIG. 6, remote-most end 52 of shaft 16 engages a slot 78 formed in second tuft block 36 to drive tuft block 36 in oscillating fashion along a plane extending substantially perpendicular to longitudinal axis 54 and first surface 18, as described above with respect to first tuft block 28 in FIG. 3.

Figure 7:
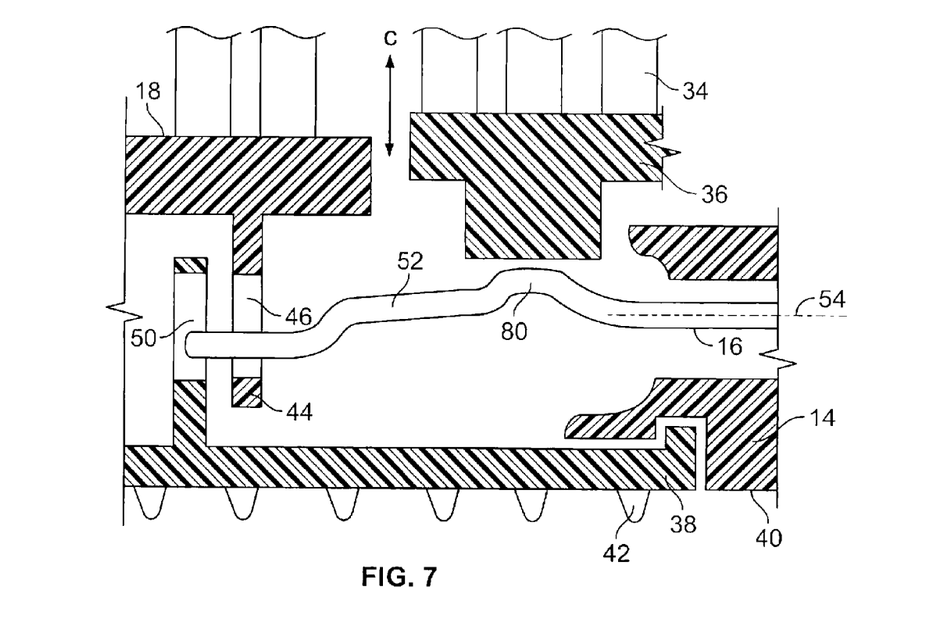
FIG. 7 is a section view of a portion of a further alternative embodiment of a head of the toothbrush of FIG. 1.

In yet another embodiment shown in FIG. 7, second tuft block 36 is driven in linear oscillating fashion in a direction extending substantially perpendicular to longitudinal axis 54 and first surface in the direction of arrow C. In such an embodiment, remote-most end 52 of shaft 16 may include a second offset portion 80 that engages a lower surface of second tuft block 36 as shaft 16 rotates, thereby moving second tuft block upwardly and downwardly with respect to head 14.

Thus, it can be appreciated that second tuft block 36 can be configured such that it is driven in an oscillating manner in many different directions. Other directions and accompanying suitable structures for providing such directional movement will become readily apparent to those skilled in the art, given the benefit of this disclosure.

Figure 8:
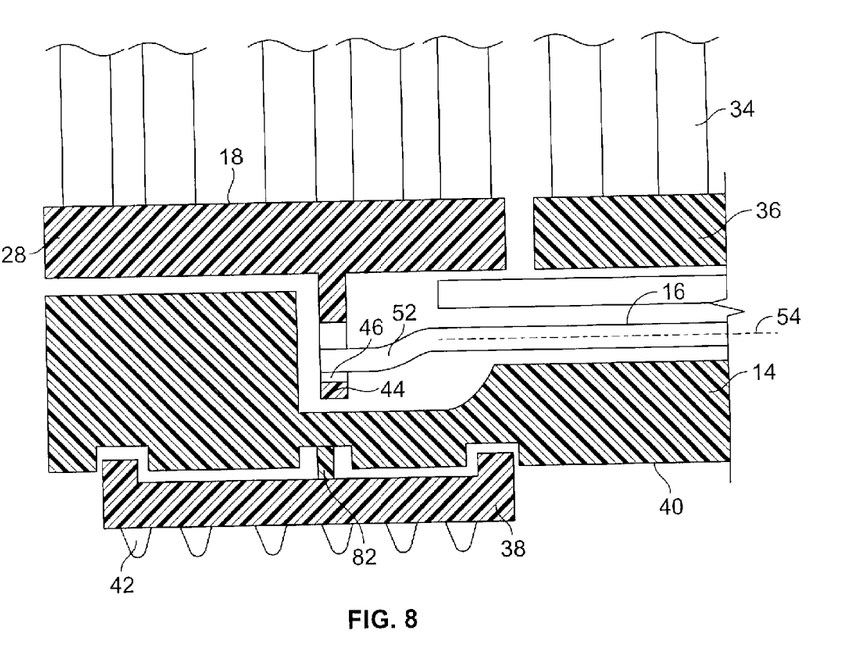
FIG. 8 is a section view of a portion of yet another alternative embodiment of a head of the toothbrush of FIG. 1.

In certain embodiments, as shown in FIG. 8, tissue cleanser 38 is movable with respect to head 14, but it is not directly connected to drive shaft 16. Tissue cleanser 38 is flexibly connected to head 14 by connecting member 82. Connecting member 82 resiliently attaches tissue cleanser 38 to head 14 so that tissue cleanser 38 is free to move or vibrate with respect to head 14. Thus as shaft 16 rotates and oscillates first tuft block 28, the resultant vibration causes tissue cleanser 38 to move or vibrate with respect to head 14. Connecting member 82 may be any type of flexible or resilient member that allows movement of tissue cleanser 38 with respect to head 14. Connecting member 82 may be, for example, formed of an elastomeric or rubber material. In other embodiments, connecting member 82 may be a spring or other resilient member. Connecting member 82 may be configured so as to provide any desired motion for tissue cleanser 36, such as left to right, up and down, rocking, bouncing, vibrating, etc. Other suitable constructions for connecting member 82 will become readily apparent to those skilled in the art, given the benefit of this disclosure.

In light of the foregoing disclosure of the invention and description of various embodiments, those skilled in this area of technology will readily understand that various modifications and adaptations can be made without departing from the scope and spirit of the invention. All such modifications and adaptations are intended to be covered by the following claims.

The invention claimed is:

1. A powered toothbrush comprising:
   a handle having a neck;
   a head mounted to the neck and having a first surface and an opposed second surface;
   a first tuft block mounted to the head, the tuft block having tooth cleaning elements extending outwardly from the first surface;
   a tissue cleanser mounted to the head and having a plurality of tissue engaging elements extending outwardly from the second surface;
   a drive assembly configured to cause the first tuft block and the tissue cleanser to move with respect to the head.

2. The powered toothbrush of claim 1, wherein the drive assembly is operably connected to at least one of the first tuft block and the tissue cleanser to drive the at least one of the first tuft block and tissue cleanser in an oscillating manner.

3. The powered toothbrush of claim 1, wherein the drive assembly comprises a power source, and a motor having a shaft with an offset portion.

4. The powered toothbrush of claim 3, wherein the power source is a battery.

5. The powered toothbrush of claim 3, wherein the first tuft block comprises a tuft block base portion having a first slot formed therein; the tissue cleanser includes a tissue cleanser base portion having a first slot formed therein; and the offset portion extends into the first slots of the tuft block base portion and the tissue cleanser base portion.

6. The powered toothbrush of claim 5, wherein the tuft block base portion has a cylindrical shape and the tissue cleanser base portion has a cylindrical shape, and the tuft block base portion and tissue cleanser base portion are nested together concentrically.

7. The powered toothbrush of claim 5, wherein the tuft block base portion includes a second slot, the tissue cleanser includes a second slot, and the head includes an aperture, and further comprising a pin that extends through the aperture in the head and into the second slots of the tuft block base portion and the tissue cleanser base portion.

8. The powered toothbrush of claim 1, further comprising a second tuft block proximate the first tuft block.

9. The powered toothbrush of claim 8, wherein the second tuft block is movable with respect to the head.

10. The powered toothbrush of claim 8, wherein the drive assembly is operably connected to the second tuft block to drive the second tuft block in an oscillating manner.

11. The powered toothbrush of claim 1, wherein the tissue engaging elements are nubs.

12. The powered toothbrush of claim 1, wherein the tooth cleaning elements are bristles.

13. The powered toothbrush of claim 1, wherein the first tuft block includes an inner ring of tooth cleaning elements and an outer ring of tooth cleaning elements.

14. The powered toothbrush of claim 13, wherein the outer ring and inner ring are driven by the drive assembly in an oscillating manner in opposite directions.

15. A powered toothbrush comprising:
a handle having a neck;
a head mounted to the neck and having a first surface and an opposed second surface;
a first tuft block mounted to the head, the first tuft block having tooth cleaning elements extending outwardly from the first surface and a tuft block base portion having a first slot formed therein;
a tissue cleanser mounted to the head and having a plurality of projections extending outwardly from the second surface and a tissue cleanser base portion having a second slot formed therein;
a power source mounted inside the handle;
a motor operably connected to the power source;
a drive shaft rotatably driven by the motor and having an offset portion that engages each of the slots of the tuft block base portion and tissue cleanser base portion to drive the first tuft block and tissue cleanser in an oscillating manner.

16. The powered toothbrush of claim 15, wherein the tuft block base portion has a cylindrical shape and the tissue cleanser base portion has a cylindrical shape, and the tuft block base portion and tissue cleanser base portion are nested together concentrically.

17. The powered toothbrush of claim 15, wherein the tuft block base portion includes a second slot, the tissue cleanser includes a second slot, and the head includes an aperture, and further comprising a pin that extends through the aperture in the head and into the second slots of the tuft block base portion and the tissue cleanser base portion.

18. The powered toothbrush of claim 15, further comprising a second tuft block proximate the first tuft block.

19. The powered toothbrush of claim 18, wherein the second tuft block is movable with respect to the head.

20. The powered toothbrush of claim 18, wherein the shaft engages the second tuft block to drive the second tuft block in an oscillating manner.

21. The powered toothbrush of claim 15, wherein the tissue engaging elements are nubs.

22. The powered toothbrush of claim 15, wherein the tooth cleaning elements are bristles.

23. A powered toothbrush comprising:
a handle having a neck;
a head mounted to the neck and having a first surface and an opposed second surface;
a first tuft block mounted to the head, the first tuft block having bristles extending outwardly from the first surface and a tuft block base portion having a first slot formed therein;
a tissue cleanser mounted to the head and having a plurality of nubs extending outwardly from the second surface and a tissue cleanser base portion having a second slot formed therein;
a battery mounted inside the handle;
a motor operably connected to the battery;
a drive shaft rotatably driven by the motor and having an offset portion that engages each of the slots of the tuft block base portion and tissue cleanser base portion to drive the first tuft block and tissue cleanser in an oscillating manner.

* * * * *